United States Patent [19]
Dennison et al.

[11] Patent Number: 5,922,616
[45] Date of Patent: Jul. 13, 1999

[54] BIOCHEMICAL SENSOR AND NOVEL MEDIA FOR BIOELECTROCHEMICAL REACTIONS

[75] Inventors: Manus Joseph Dennison; Jennifer Maeve Hall; Anthony Peter Francis Turner, all of Bedfordshire, United Kingdom

[73] Assignee: Cranfield University, Bedfordshire, United Kingdom

[21] Appl. No.: 08/836,891

[22] PCT Filed: Nov. 23, 1995

[86] PCT No.: PCT/GB95/02742

§ 371 Date: May 22, 1997

§ 102(e) Date: May 22, 1997

[87] PCT Pub. No.: WO96/16185

PCT Pub. Date: May 30, 1996

[30] Foreign Application Priority Data

Nov. 23, 1994 [GB] United Kingdom ............... 9424125

[51] Int. Cl.[6] .................................................. G01N 33/543
[52] U.S. Cl. .......................... 436/518; 204/400; 204/403; 204/414; 204/424; 422/55; 422/57; 422/68.1; 422/82.05; 422/83; 422/88; 435/287.1; 435/287.2; 435/287.5; 435/288.7; 435/807; 435/808; 436/149; 436/164; 436/524; 436/527; 436/525; 436/805; 436/806; 436/807
[58] Field of Search .............................. 422/55, 57, 68.1, 422/83, 88, 82.05; 435/287.1, 287.2, 287.5, 288.7, 807, 808; 436/518, 524, 527, 525, 805, 807, 149, 164, 806; 204/400, 403, 414, 424

[56] References Cited

U.S. PATENT DOCUMENTS 4,925,544  5/1990  Goldring ................................. 204/421
5,154,808  10/1992  Miyasaka et al. .
5,212,050  5/1993  Mier et al. ............................. 430/320

FOREIGN PATENT DOCUMENTS

| | | |
|---|---|---|
| 0 255 291 A1 | 2/1988 | European Pat. Off. . |
| 0 585 113 A2 | 3/1994 | European Pat. Off. . |
| 0 634 488 A2 | 1/1995 | European Pat. Off. . |
| 0 636 879 A2 | 2/1995 | European Pat. Off. . |
| 40 32 599 A1 | 4/1992 | Germany . |
| 1571282 | 7/1980 | United Kingdom . |
| WO 88/01299 | 2/1988 | WIPO . |
| WO 89/04364 | 5/1989 | WIPO . |

OTHER PUBLICATIONS

J. Wang et al., "Organic–Phase Enzyme Electrode For the Determination of Trace Water in Nonaqueous Media", *Anal Chem.*, vol. 54, pp. 845–847 (1993).

M. Dennison et al., "Gas–Phase Microbiosensor For Monitoring Phenol Vapor AT ppb Levels", *Anal. Chem.*, vol. 67, pp. 3922–3927 (1995).

T. Okada et al., "Microbial Sensor System Which Uses Methylomonas sp. For the Determination of Methane", *European J. Appl. Microbiol Biotechnol*, vol. 12, pp. 102–106, (1981).

L. Goodson et al., "Application of Immobilized Enzymes to Detection and Monitoring", *Midwest Research Institute*, pp. 393–400.

*Primary Examiner*—Christopher L. Chin
*Attorney, Agent, or Firm*—Oliff & Berridge, PLC

[57] ABSTRACT

The invention provides a sensor for detecting an analyte comprising a support for a bioreceptor or biomimic and a detection means, wherein the support can retain a bioreceptor or biomimic and the support and the bioreceptor or biomimic and the detection means can be arranged such that when the sensor is placed in a medium containing a substrate, the substrate contacts the bioreceptor or biomimic and reacts to generate a response which is detectable by the detection means and which is relatable to the concentration of the analyte, and the support comprises a non-volatile organic liquid.

29 Claims, 8 Drawing Sheets

BIOCHEMICAL SENSOR AND NOVEL MEDIA FOR BIOELECTROCHEMICAL REACTIONS

This invention relates to a sensor for detecting chemical compounds in particular in the gaseous or vapour phase. The invention also relates to novel media for biochemical reactions and a method for monitoring an analyte by determining a biocatalytic reaction of a substrate with a bioreceptor or biomimic, the concentration of the analyte being relatable to that of the substrate.

Many gas sensors are known. They often suffer from lack of specificity and one method for overcoming such lack of specificity is to incorporate a catalyst or biological catalyst, even whole bacteria, which usually have high specificity.

In DE-A-4032599 a non-biological gas sensor is described. A three dimensional polyurethane matrix containing an electrolyte and a catalyst is positioned at a test electrode. The current generated between the test electrode and a second, counter electrode is dependent upon the partial pressure of the test components. However, this reference does not relate to bioelectrochemical reactions and therefore the specific requirements for maintaining a bioreceptor or biomimic in an active state.

Generally reactions monitored using biological catalysts are carried out in bulk aqueous solution. This is largely because in order to maintain the activity of a bioreceptor and sometimes a biomimic, a hydration shell is needed around the bioreceptor or biomimic. This is essential to retain the three dimensional structure of the bioreceptor or biomimic which in turn is essential for its activity. In these types of sensor, generally an analyte for detection must be dissolved in solution in the bulk aqueous liquid prior to detection.

However, gas sensors based on bulk aqueous liquids have inherent short-comings: limited shelf life due to solvent evaporation and, a particular problem when detection is electrochemically, electrode corrosion.

In solution biocatalytic activity may even result in damaged seals and eventually cause leakage of the bulk liquid.

In European J. Appl. Microbiol. Biotechnol (1981) 12:102–106, Okada et al describe a biological methane gas sensor in which bacteria are immobilised in acetylcellulose filters with agar gel and their respiration is monitored using an oxygen electrode. However, such detectors detect only the respiration activity of the bacteria and not the reaction of an enzyme with its substrate. It would be desirable to detect the reaction itself as this would confer increased sensitivity on an apparatus.

It is also known to use detection of an analyte using enzymes in a bulk liquid medium which is not an aqueous liquid. For example, reactions in organic or micro-aqueous solvents are monitored by the method of apparatus as described in WO89/04364. In this publication, enzymes are retained at a support on an electrode by either covalent bonding or by hydrophilic attraction to a membrane comprising polymeric material and the electrode is immersed in the bulk solvent medium. This method does not detect a gaseous or vapour phase analyte.

It is also known to use as the support material, for the enzyme, a solid/gel phase comprising for example an inorganic salt, as is described in European patent application No. 93306738.1. Organic or inorganic solid supports for enzymes are also described in WO88/01299. This disclosure relates to a sensor which monitors a colour change to indicate the presence of a reaction due to the presence of a substrate for the enzyme. The enzyme support disclosed does not therefore need to be conducting and micro crystalline cellulose is the only example given.

L. H. Goodson and W. B. Jacobs, in Enzyme Engineering Ballstock 2, Plenum Press, New York, 974, page 393 edited by E. K. Pye and L. B. Wingard Jr. describe immobilised enzymes for detecting the presence of an enzyme inhibitor by electrochemical means. The enzymes are immobilised trapped in starch gel on the surface of open pore polyurethane foam. It is reported that the open pore structure of the polyurethane foam is used because it enables both air and liquid to pass through simultaneously to enable the substrate for the enzyme to contact the enzyme and react.

However, solid support materials may tend to be problematic in that evaporation of water vapour may tend to occur to a point below the essential degree of hydration of the enzyme or other bioreceptor or biomimic, so that it loses activity.

The present inventors have found novel support media in which a bioreceptor or biomimic can be retained and which enables maintenance of improved stability of the bioreceptor or biomimic, partly due to the relatively stable degree of hydration of the media which can be maintained for prolonged periods. The invention also therefore, provides improved media for use in biocatalytic sensors.

In accordance with the present invention there is provided a sensor for detecting an analyte comprising a support for a bioreceptor or biomimic and a detection means, the support retaining a bioreceptor or biomimic and the support, bioreceptor or biomimic and detection means being arranged such that in use, the sensor is placed in a medium containing a substrate, the substrate contacts the bioreceptor or biomimic and reacts, generating a response detectable by the detection means, the response being relatable to the concentration of the analyte, characterised in that the support comprises a non-volatile organic liquid.

The detection means may comprise any indicator or instrumental method which will enable visual or other detection of the presence or absence of a reaction between the bioreceptor or biomimic and the substrate, to enable detection of an analyte which is the substrate or a substrate pre-cursor, or an inhibitor or precursor for an inhibitor of the bioreceptor or biomimic.

For example, as described in WO88/01299, the detection means may comprise a colour indicator which will be incorporated into or in contact with the support.

One preferred detection means comprise electrochemical detection.

In accordance with a preferred embodiment of the present invention, there is provided an electrode sensor for detecting an analyte comprising a conductor, a support for a bioreceptor or biomimic contacting the conductor and a bioreceptor or biomimic retained at the support, the conductor, support and bioreceptor or biomimic being arranged such that in use, when the electrode is placed in a medium containing a substrate, the substrate contacts the bioreceptor or biomimic and reacts, generating an electrical response for detection, the response being relatable to the concentration of the analyte, characterised in that the support comprises a non-volatile organic liquid. Preferably the support consists essentially only of a non-volatile organic liquid.

The electrode may be any electrode which can be used in an electrochemical cell, but is preferably a microelectrode because internal resistance (IR drop) is minimised in a microelectrode, resulting in an improved signal to noise ratio over conventional electrodes.

The electrode configuration may be that of any electrochemical cell. The gas sensor of the present invention may be a two electrode sensor in which there is a sensing electrode and a counter electrode which also acts as a reference electrode. However if the counter electrode tends to polarise with current, preferably the sensor will be a three electrode sensor comprising the sensing electrode, and separate counter and reference electrodes respectively.

Preferably, the rate of access of analyte is restricted to the electrode in the sensor, by a diffusion barrier, as described in GB1571282, under conditions such that the electrode is operating in a so-called limiting current region. In the limiting current region, the concentration of the analyte at the electrode surface is essentially zero. The limiting current will then be proportional to the flux of the analyte which will be a function of the partial pressure of the analyte in the gas being sensed.

Thus, in a preferred embodiment of the invention where the sensor is as described above and the support is provided with a porous membrane which substantially covers the support, the membrane may be used to limit the rate of mass transfer of the gaseous or vapour analyte to the bioreceptor or biomimic to ensure that that is the rate limiting step in the monitoring.

Such a diffusion barrier may produce the additional advantage that it will result in increased stability of the support and therefore in the performance of the gas sensor.

When the gas sensor is being used to detect an inhibitor for the bioreceptor or biomimic it may be decided that the biosensor should not operate in the limiting current range and that instead, the rate limiting step may be the rate of catalysis. In this case, for an inhibitor analyte the rate of inhibition will provide the rate limiting step and not the rate of mass transfer.

Thus, the present invention provides a biosensor for direct detection of an analyte, in particular a gaseous or vapour phase analyte. Because the apparatus detects a response due to an electrical or other change directly related to the reaction between the bioreceptor or biomimic and the substrate for the bioreceptor or biomimic, the apparatus requires no pre-concentration or pre-measurement calibration step. In addition, the present invention is advantageous because useful results may be obtained using very low sample volumes of gas or vapour. For example, an analyte may be detected from gaseous volumes as low as 1 $cm^3$ or below. Rapid results are obtained so that detection of the analyte can be indicated within, for example, 100 seconds or 50 seconds but even more rapid results are feasible. The results are immediate and no laboratory analysis is needed.

The invention also relates to an electrode sensor for detecting an analyte comprising a conductor, in support for a bioreceptor or a biomimic contacting the conductor and a bioreceptor or biomimic retained in the support, the conductor, the support and bioreceptor or biomimic being arranged such that in use, when the electrode is placed in a medium containing a substrate, the substrate contacts the bioreceptor or biomimic and reacts, generating an electrical response for detection, the response being relatable to the concentration of the analyte characterised in that the support comprises a non-volatile organic liquid having an affinity for the analyte.

The invention also relates to a method for detecting analyte comprising contacting a medium comprising the analyte with the sensor as defined above whereby the substrate contacts the bioreceptor or biomimic and reacts, generating a response and measuring the response of the cell, the response being relatable to the concentration of the analyte.

A particular problem with previous gas phase biosensors is that dehydration of the support medium for the enzyme rapidly occurs, producing varying results and after a relatively short time, the bioreceptor or biomimic may be inactivated. The present invention is particularly advantageous because the organic liquid used substantially reduces the rate of evaporation of water from the liquid so that more uniform results and greater stability of the apparatus are obtained. In addition, it has been found that using an organic liquid, the water content in the organic liquid may tend to equilibrate at a particular atmospheric humidity and therefore after exposing the gas sensor to a particular atmosphere for sufficient time to allow the water content in the support to equilibrate, good, constant performance of the gas sensor can be achieved, which is not adversely affected by dehydration of the support.

In the method of the invention, preferably the support of the sensor is allowed to equilibrate to the relative humidity of the environment in which it is to be used for at least 1 minute, preferably at least 1.5 minutes and most preferably at least 2 minutes, prior to contact with the analyte.

The analyte may be for example a binding protein for a bioreceptor or any other reactant or reactant precursor which will produce a detectable, preferably electrochemical, reaction. Alternatively, the analyte may be an inhibitor or precursor for an inhibitor for the bioreceptor or biomimic.

The substrate may be the analyte or it may be produced from a reaction of the analyte at or in the support. Thus, one possibility is that the substrate undergoes reaction at the electrode under the influence of the bioreceptor or biomimic. An alternative is that the enzyme catalyses the conversion of the substrate into a product which then undergoes an electrochemical reaction directly at the electrode. A further alternative is that the bioreceptor or biomimic is one that can effect oxidation or reduction of the substrate, optionally with the intervention of a mediator, so that transfer of electrons between the substrate and the electrode occurs.

The bio-receptor or biomimic can be any biological molecule which will bind to a reactant and will produce a detectable reaction or its synthetically prepared chemical analogue (biomimic), for example a synzyme. Examples of bioreceptors are antibodies, binding proteins and biological catalysts such as enzymes. The bioreceptor or biomimic will generally be a biological catalyst such as an enzyme or synthetic equivalent thereof. When the bioreceptor or biomimic is an enzyme, or synthetic equivalent thereof, the substrate can be an enzyme-substrate or an enzyme-cofactor. The enzyme may be present as a component of a whole cell, cell membrane or organelle, or as a purified substance.

The non-volatile organic liquid substantially does not evaporate off during conditions of use of the sensor or does not evaporate to an extent to which it becomes ineffective over the time period for monitoring. Preferably the vapour pressure of the organic liquid will be no greater than 18 mmHg at 20° C., most preferably no greater than 10 mmHg or even 8 mmHg at 20° C. Generally the boiling point of the liquid will be above 110° C. or 150° C. or even above 180° C. or 200° C. at atmospheric pressure. The liquid may be held on the electrode for example, by forming a depression on the electrode but is generally held as a fine liquid layer.

The conditions of use will generally be at atmospheric pressure and temperatures of from 0 to 40° C.

One method for helping to retain the liquid on the electrode is to use a viscous organic liquid, for example having a viscosity of at least 10 centipoises or even at least 75 cps (at 20° C.). If desired a thickener may be added such as an alginate or cellulose fibres.

The viscosity of the organic liquid may be used to ensure that the support will be in the form of a relatively thin layer such as a coating on a base plate or on an electrode (for electrochemical monitoring), in use. A protective gas permeable mesh or membrane may be positioned over the film on the electrode. Generally the coating of viscous liquid on the electrode will be no greater than 5 mm thick, preferably no greater than 3 mm thick and most preferably no greater than 1mm or 0.5 mm thick, often no greater than 0.4 mm or 0.3 mm thick. Layers of support which are no greater than 200 $\mu$m or 100 $\mu$m or even 50 $\mu$m thick also provide good results. Whilst thicker coatings of organic liquid may be used, at greater thicknesses, greater viscosity may be required to result in a layer which will not flow from the electrode during use. Furthermore, at greater thicknesses little additional advantage is obtained and the sensitivity of the sensor may be reduced.

The organic liquid support will include sufficient water to provide a hydration shell around the bioreceptor or biomimic to retain activity. Generally, there should be at least 2% by weight (based on the weight of the organic liquid alone) water, preferably at least 5%, where a hydration shell is required. Preferably the water content is not too high, as high water content tends to adversely affect the longevity of the bioreceptor or biomimic. For example, the organic liquid may contain up to 100%, often up to 60%, preferably up to 50%, by weight (based on the weight of the organic liquid alone) water, preferably up to 40% and most preferably up to 25%, or 10% by weight water. Preferably the organic liquid is water miscible.

The affinity of the organic liquid support for the analyte may be for example because the organic liquid is soluble in the analyte or the analyte is soluble in the organic liquid. A particularly preferred organic liquid is glycerol. Glycerol has been found to be particularly advantageous because phenols are soluble in it and will therefore tend to absorb phenolic vapours which can be detected using a polyphenol oxidase enzyme. Hydrogen sulphide, hydrogen cyanide, and sulphur dioxide are also very soluble in glycerol and can therefore be detected using a sensor according to the present invention.

The novel support media of the invention are able to maintain activity of the bioreceptor or biomimic, provide electrical conductivity and are sufficiently permeable to enable the reactant for the reaction with the bioreceptor or biomimic to reach the bioreceptor or biomimic and react. The mass transfer properties through the liquid enables the gaseous or vapour substrate to permeate and contact the bioreceptor or biomimic.

For electrochemical monitoring, an electrolyte may be incorporated into the support liquid but it has been found that in particular when a micro-electrode is used, even in the absence of added electrolyte, electrical activity is detected and it is postulated that this is due to mobility of hydrogen and hydroxyl ions within the organic liquid.

Optionally, the support may also include a buffer for the bioreceptor or biomimic if required. The incorporation of such a buffer may be advantageous as it may prolong the life of a bioreceptor or biomimic for example where the bioreceptor or biomimic is a biological catalyst.

An enzyme mediator compound may optionally also be included in the support liquid for example, where the reaction to be monitored uses such a mediator, for example potassium ferricyanide which can be oxidised to ferrocyanide and can be reduced back to ferricyanide at an electrode. If it is desired to change the water content of the organic liquid support, a hygroscopic material may optionally also be incorporated in the liquid, for example lithium chloride. Addition of a known amount of a hygroscopic compound such as lithium chloride will result in a known associated addition of water, to the support. The organic liquid itself may be hygroscopic. By hygroscopic as used herein with reference to a particular material is meant that the material takes up moisture in sufficient amount that there is no net moisture loss due to drying.

Examples of suitable applications for the sensors of the present invention include for example detection of sulphur dioxide, using a sulphite oxidase enzyme, detection of phenolic vapour using a polyphenol oxidase, detection of vapours of ethanol and other alcohols, using alcohol oxidase enzyme, detection of methane using an oxygenase enzyme (or biomimic), detecting organic compounds such as hydrocarbons eg camphor using cytochrome P450 or synthetic analogue, detecting NOx gases using nitrate reductase, detecting carbon monoxide using carbon monoxide oxidoreductase, detecting cyanide using cytochrome oxidase, detecting TNT using TNT oxidoreductase or detecting pesticide for example using enzymes which may metabolise the analyte or antibodies.

According to a further aspect of the invention also provided is a novel support medium for a bioelectrochemical reaction comprising a non-volatile organic liquid, a biomimic or bioreceptor for the reaction being retained at the support medium and the substrate for the reaction being contactable with the support to produce the reaction, the viscous organic liquid having a boiling point above 100° C. at atmospheric pressure.

EXAMPLE 1

A phenol sensor was prepared as follows: Polyphenol oxidase (63 units) was dissolved in 0.6 μl sodium phosphate buffer (pH 7.2, 0.1 M). 2.4 μof analar grade glycerol (boiling point 290° C. at atmospheric pressure), were added to the mixture and the solution was mixed thoroughly. This mixture (3 μl) was then pipetted onto the interdigitated microelectrode area (c.15 mm$^2$) of a gold microband electrode (supplied by Microsensor Systems, Kentucky, USA). A two electrode system was used: one set of microband electrodes acting as the working electrode and the other set acting as a combined counter and quasi reference.

Figure 1:
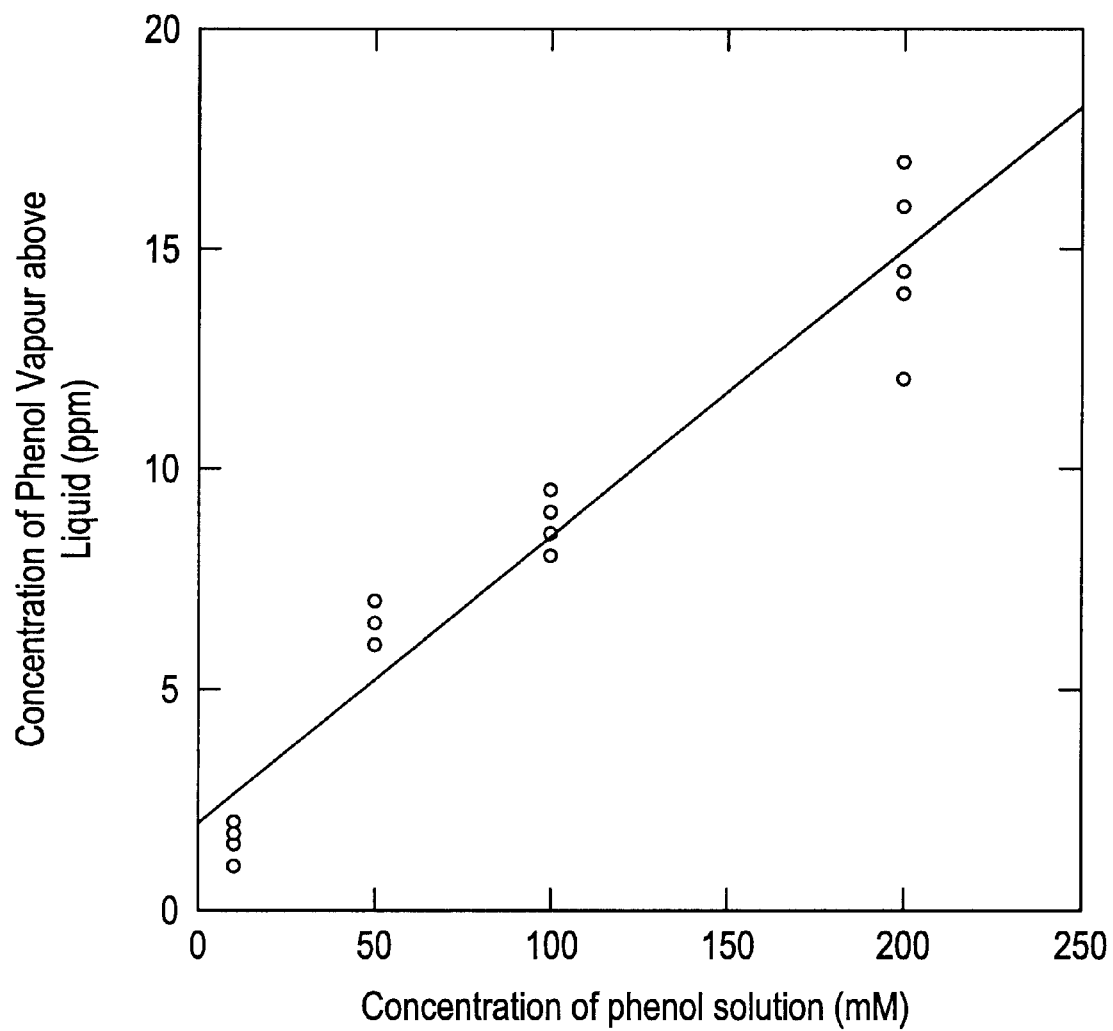
FIG. 1 is the calibration curve obtained showing the relationship between the concentration of phenol in water (mM), and the concentration of phenol vapour (ppm) above the solution. A minimum of six replicate measurements were taken of the phenol vapour concentration at each of the concentrations of the phenol solution.

The sensor was then exposed to phenol vapours by placing it in the vapour above an aqueous phenol solution of known concentration. A 100 ml amber bottle was filled with 60 ml of aqueous phenol solution and allowed to equilibrate for at least 12 hours and then for at least 45 mins between consecutive uses, in a water bath at 20.5° C. The phenol sensor was exposed to the phenol by inserting the phenol sensor approximately 1 cm into the bottle. Using a scaled up version of this (using a 10 litre bottle) a calibration curve showing the relationship between concentration of phenol in the aqueous phase and the vapour phase was constructed as illustrated in FIG. 1. This was used to establish a range of phenol vapour concentrations.

Figure 2:
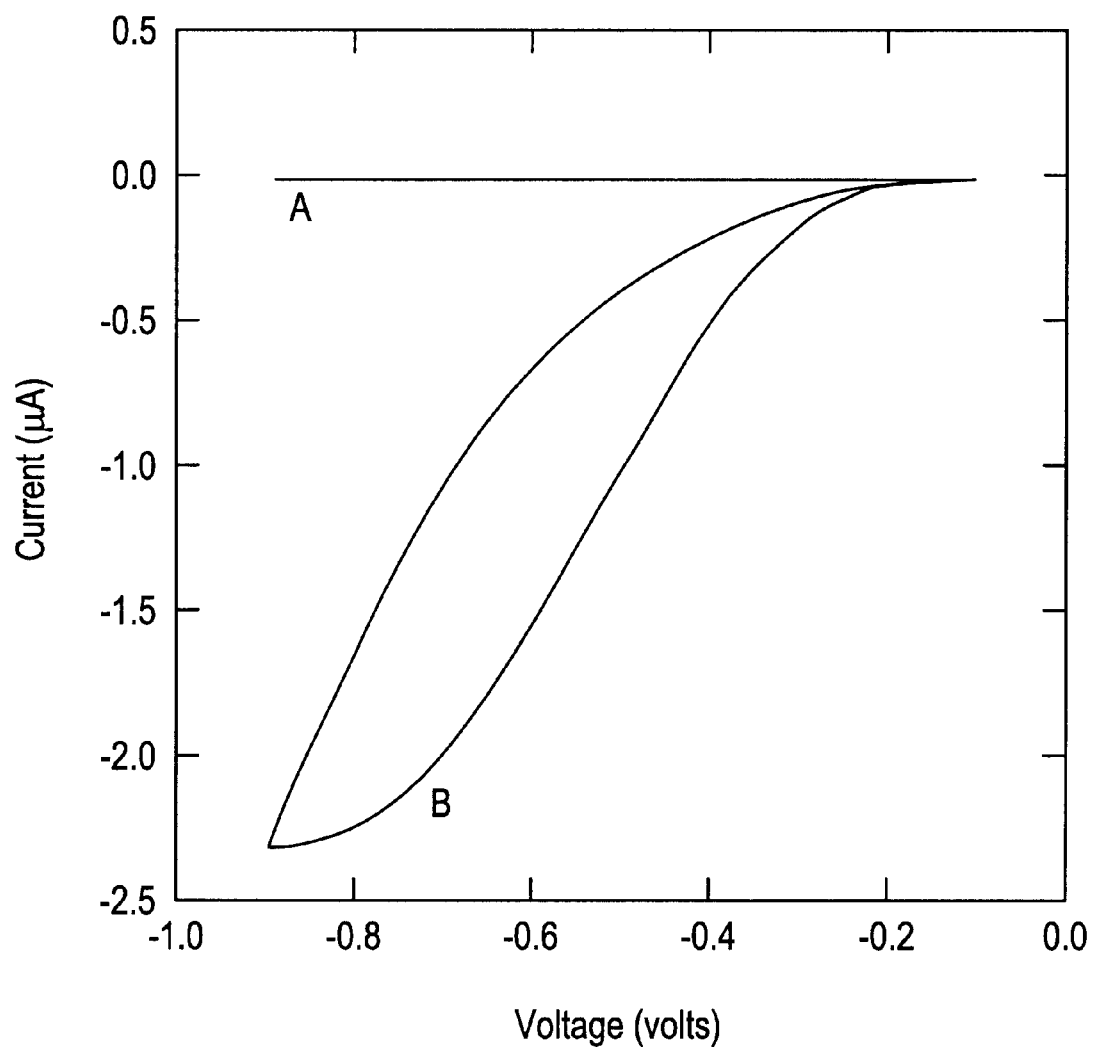
FIG. 2 is a cyclic voltagram of the phenol sensor in the absence (A) and presence (B) of approximately 8.5 ppm phenol vapour. The measurements were taken at a scan rate of 0.005 V/s.

Results:
Cyclic Voltammogram—FIG. 2

A phenol sensor was prepared as described above. A cyclic voltammogram in the absence of phenol vapours showed no peaks, but on exposure to phenol vapours (approximately 8.5 ppm) a large increase in current in the range −600 mV to −800 m V can be seen. This increase is attributed to the reduction of the product of phenol oxidation, benzoquinone, at the electrode.

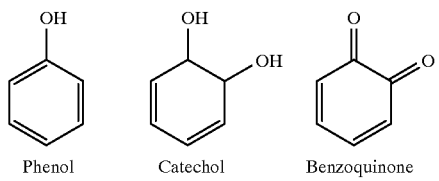

Phenol    Catechol    Benzoquinone

Figure 3:
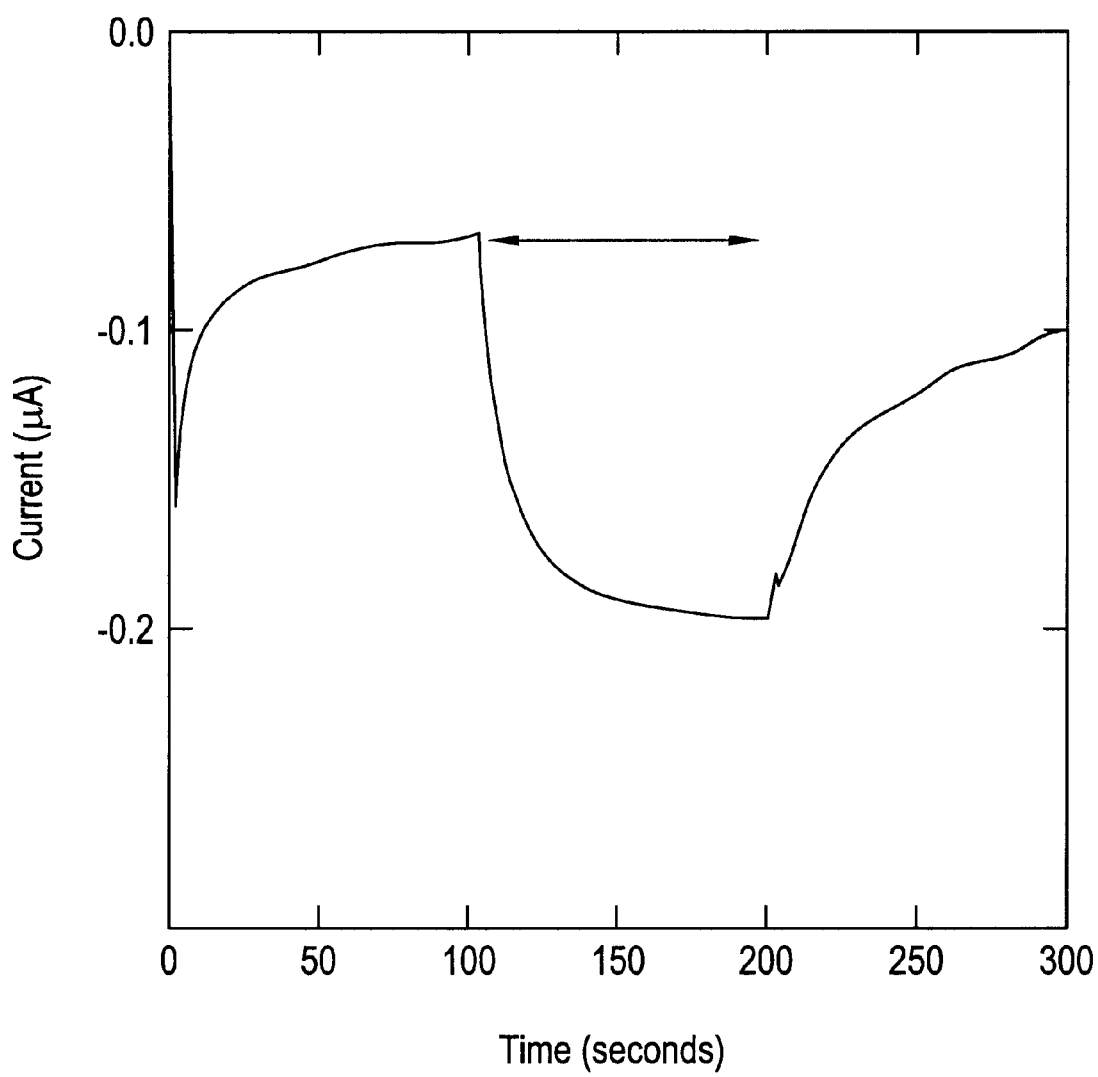
FIG. 3 shows the amperometric response of a phenol sensor on exposure to 1.6 ppm phenol vapour for 100 seconds. The arrow indicates the period of exposure.

Amperometric Response—FIG. 3

A phenol sensor was prepared as described above and poised at −700 mV. On exposure to approximately 1.6 ppm phenol vapour, an increase in current was recorded (FIG. 3).

Phenol molecules in the atmosphere readily dissolve into the glycerol matrix. Here they are oxidised to benzoquinone by polyphenol oxidase. Benzoquinone is readily reduced at the electrode surface, generating an electrochemical signal. On removal of the phenol vapour the current declines, eventually to background levels, corresponding to a decrease in benzoquinone at the electrode surface.

Figure 4:
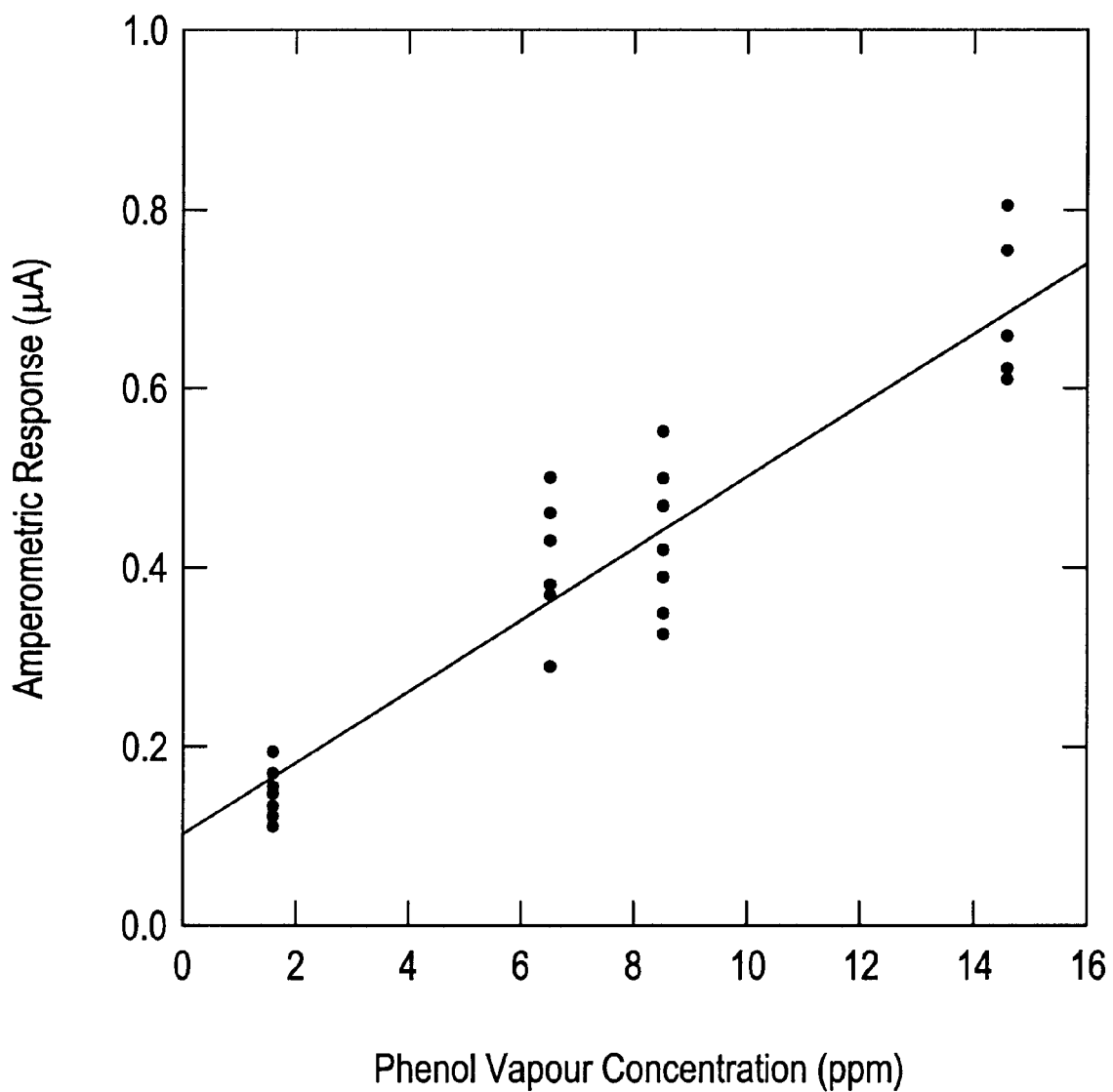
FIG. 4 shows the amperometric response of a phenol sensor on exposure to different phenol vapour concentrations for 100 seconds. Each time, the sensor used was exposed to a phenol vapour concentration for 100 s and the amperometric response was recorded. Each data point is the response of one freshly prepared sensor on exposure to the shown vapour concentration for 100s.

Calibration curve—FIG. 4

Phenol sensors were prepared as outlined above, and were poised at −700 mV. They were then exposed to a range of phenol vapour concentrations (FIG. 4). Each data point is the amperometric response of a freshly prepared phenol sensor on exposure to the shown phenol vapour concentration for 100 seconds.

Figure 5:
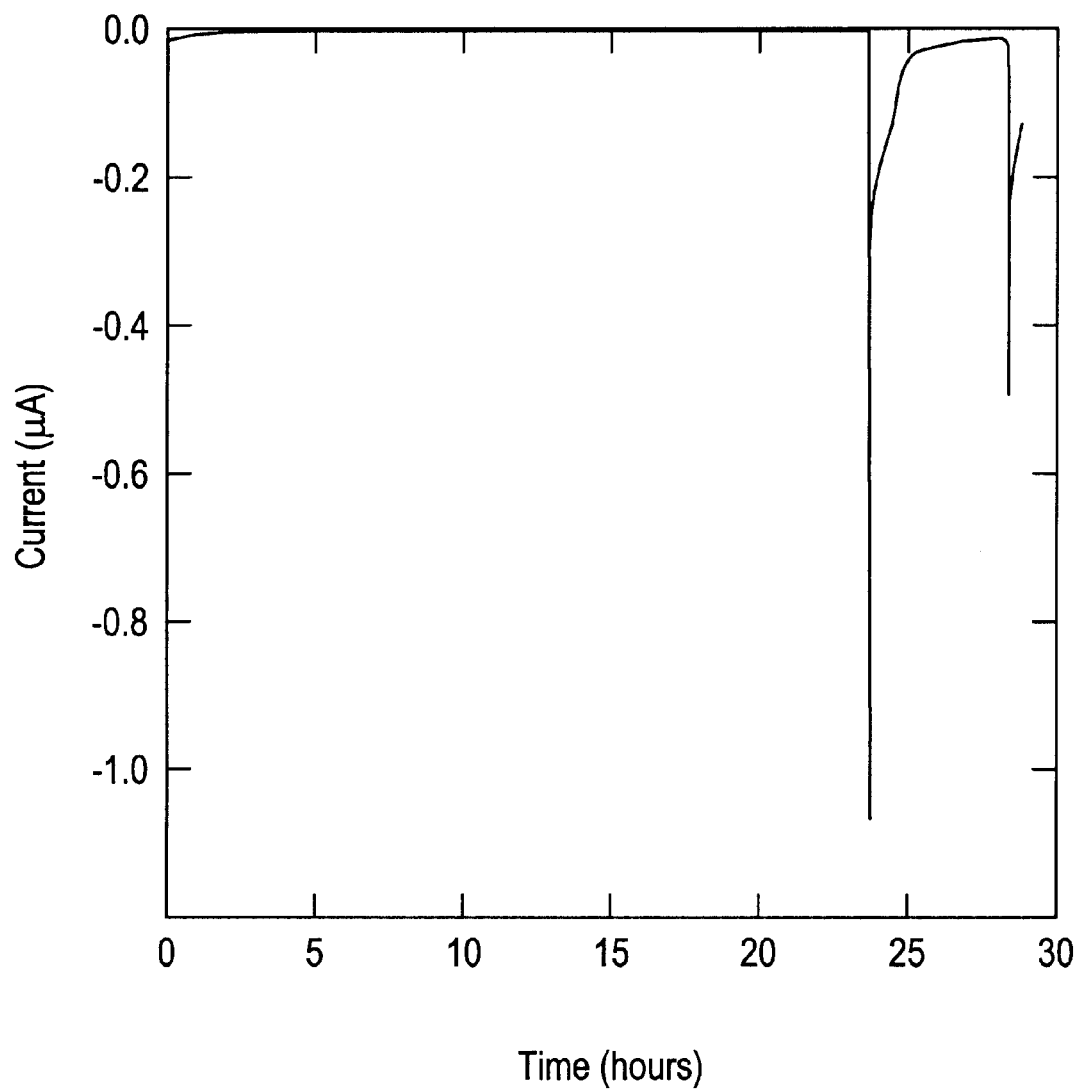
FIG. 5 shows 27 hour on-line monitoring for phenol using a phenol sensor. At T=23.6 hrs and T=28.3 hrs the phenol sensor was exposed to approximately 8.5 ppm phenol for 200s and 100s periods respectively.

Online monitoring for 27 hours—FIG. 5

A phenol sensor was prepared as outlined above, and was poised at −700 mV for 28.8 hours. At 23.6 hours and 28.3 hours the phenol sensor was exposed to 8.5 ppm phenol vapour for 200 and 100 seconds respectively (FIG. 5). A large increase in current resulted in both cases. A control response to water vapour alone (approximately 21° C., 95% RH) showed only a very small increase in current.

Figure 6:
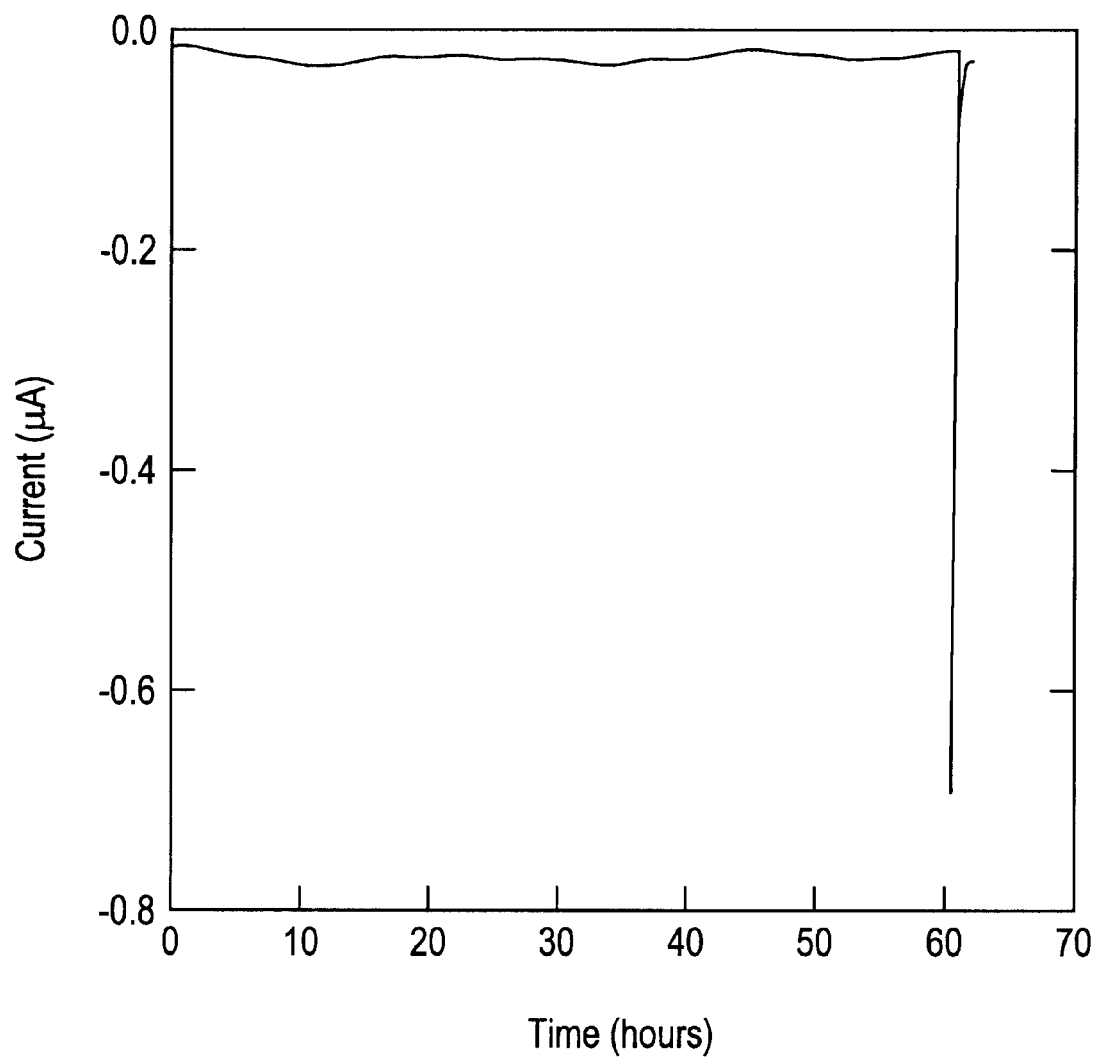
FIG. 6 shows 62 hour on-line monitoring for phenol using phenol sensor. At T=62.2 hours the phenol sensor was exposed to approximately 8.5 ppm phenol vapour for 100 seconds.

Online monitoring for 62 hours—FIG. 6

A phenol sensor was prepared as outlined above, and was poised at −700 mV for 61 hours. At 61.2 hours the sensor was exposed to 8.5 ppm phenol vapour for 100 seconds (FIG. 6). A large increase in current resulted.

This Example shows how low concentrations of phenol were detected using a biosensor according to the present invention.

EXAMPLE 2

An ethanol sensor was prepared in the same manner as the phenol sensor of example 1, except that alcohol oxidase (AOX) was used instead of polyphenol oxidase and the buffer and glycerol were used in a ratio of 1:1 by volume and the electrode system comprised a combined counter and Ag/AgCl reference electrode and a graphite working electrode.

Results:
Amerometric Response to Water and to Ethanol—FIG. 7

An ethanol sensor was prepared as described in Example 2 above. The operating potential was set at +1.1 V vs Ag/AgCl. The sensor was then exposed to water vapour (approximately 95% RH) and subsequently exposed to water vapour and ethanol vapour (approximately 50 ppm ethanol). The temperature was 25° C.

The same test was carried out using a blank sensor, using BSA instead of AOX.

Figure 7:
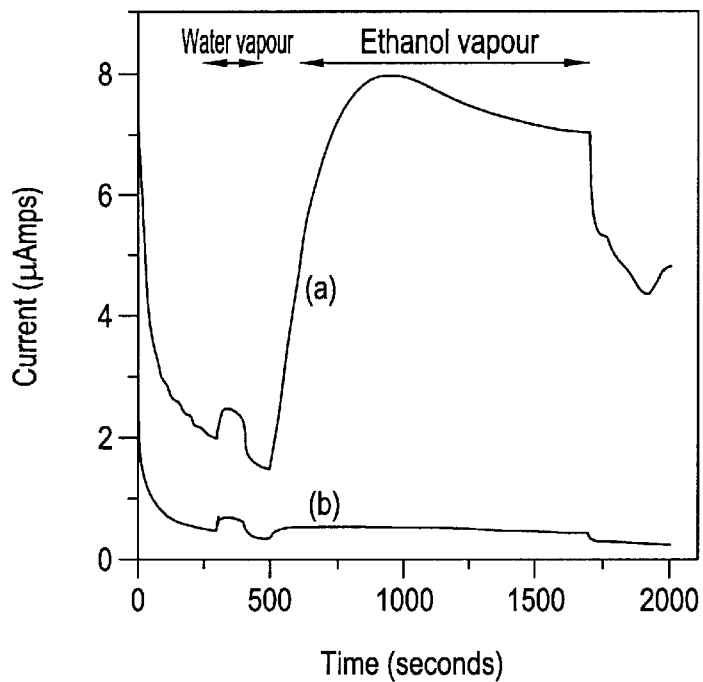
FIG. 7 shows the amperometric response of an ethanol sensor (a) and a "blank" (using BSA (bovine serum albumin) instead of alcohol oxidase) on exposure to water vapour.

Results are shown in FIG. 7, the line (a) representing the AOX sensor and the line (b) representing the blank.

The AOX sensor showed a good response to ethanol/water vapour, with steady state kinetics predominating after approximately 8 minutes. A small increase in response on exposure to water vapour was also recorded, probably due to increased mobility of ions in the buffer/glycerol gel due to water absorption or a decrease in the rate of water loss. The blank sensor showed only small increases in current on exposure to water vapour and water/ethanol vapour, again probably due to increased mobility of ions.

The reaction of the sensor is attributed to interaction between ethanol and the AOX enzyme to form hydrogen peroxide, which is an electroactive compound and can be detected amperometrically.

Figure 8:
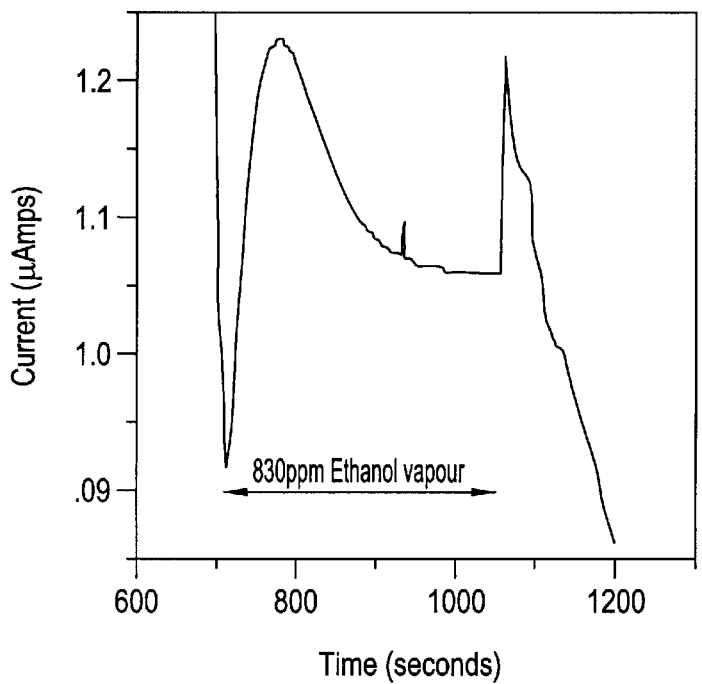
FIG. 8 shows the amperometric response of an ethanol sensor on exposure to 830 ppm ethanol vapour.

Amperometric Response to Continued Exposure—FIG. 8

An ethanol sensor was prepared as described in Example 2 above. Potential was set at +1.1 V vs Ag/AgCl. Tests were carried out at 25° C. and 70% RH.

On continuing exposure under these conditions the sensor showed a response to ethanol vapour, with steady state kinetics predominating after approximately 6.5 minutes. shown in FIG. 8.

Figure 9:
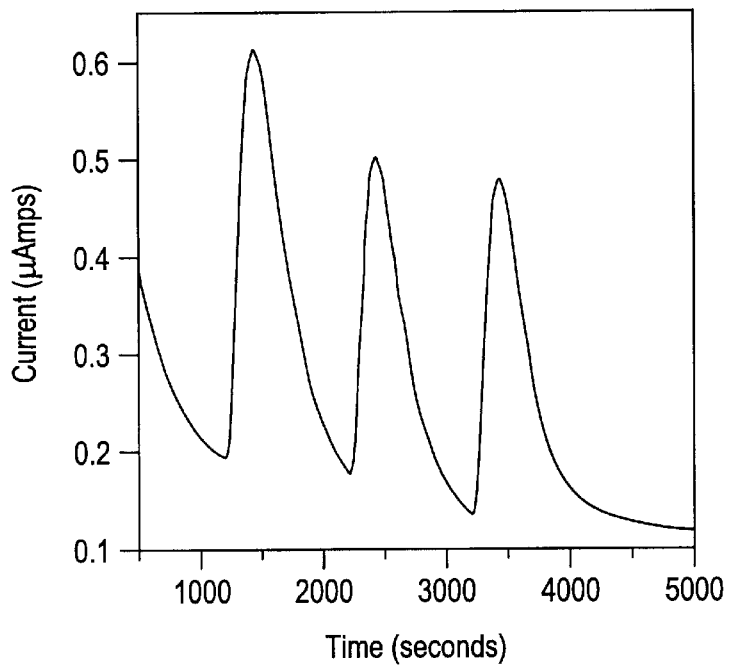
FIG. 9 shows the amperometric response of an ethanol sensor on repeated exposure to ethanol vapour (858 ppm, 780 ppm and 807 ppm). The arrows indicate the period of exposure (three periods of 100 seconds exposure).

Amperometric Response to Repeated Exposure—FIG. 9

An ethanol sensor was prepared as described in Example 2 above. The sensor was then repeatedly exposed to ethanol vapour, at 25° C. and 70% RH. The sensor was exposed to 858 ppm, 780 ppm and 807 ppm ethanol vapour, each for 100 seconds. Results are shown in FIG. 9, on which the arrows indicate the period of exposure. The repeat exposures were carried out after a sufficient time to allow the current to return to its baseline value. Consistent results were produced, the sensor showing responses of 0.42 μA, 0.33 μA and 0.35 μA for the 858 ppm, 780 ppm and 807 ppm exposures, respectively. This indicates that the ethanol sensor may be used for repetitive measurements.

Figure 10:
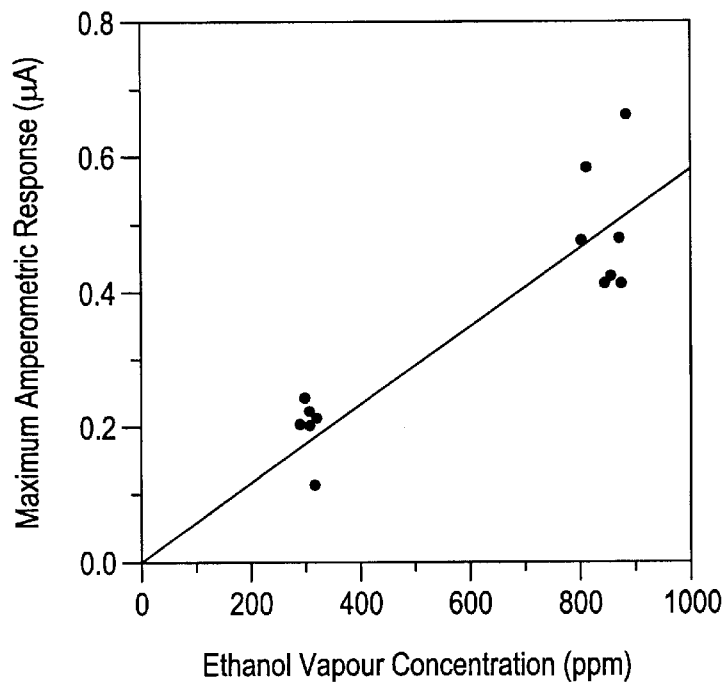
FIG. 10 shows the calibration curve of an ethanol sensor.

Calibration Curve—FIG. 10

An ethanol sensor was prepared as described in Example 2 above. It was exposed to a predetermined ethanol vapour concentration and the maximum amperometric response determined. Responses were determined for ethanol vapour concentrations over the range 0 ppm to 1000 ppm, a fresh sensor being used for each measurement. Each exposure was carried out for 100 seconds at 25° C. and 70% RH.

The calibration curve produced is shown in FIG. 10. Each point on the graph shows the response of one sensor. The relationship between the sensor response and the concentration of the ethanol vapour can be used, together with additional theoretical calculations, to enable concentration to be calculated from any given response.

EXAMPLE 3

A phenol sensor was prepared as in Example 1, using 252 units polyphenol oxidase and 80:20 glycerol:buffer (by volume). This sensor also gives good results and can show sensitivity to phenol levels as low as 29 ppb after 100s exposure at 40% RH and 25° C., and even as low as 740 ppt after longer exposure times (up to 25 hours) and at 50–60% RH and 25° C.

The success of the phenol sensor of the invention is attributed in part to a redox recycling mechanism. Such a mechanism can be applied to other aspects of the invention.

Instead of gold microband electrodes, a system comprising a gold microdisc electrode with an Ag/AgCl reference electrode may also be used for the sensors of the invention.

It will be appreciated that the physical construction of the sensors of the examples and other aspects of the invention may be conventional with the exception of the use of the specified support medium.

We claim:

1. A sensor for detecting an analyte in a gaseous or vapour phase comprising a support for a bioreceptor or biomimic and a detection means, wherein a bioreceptor or biomimic is immobilised at the support and the support and the bioreceptor or biomimic and the detection means can be arranged such that when the sensor is placed in a medium containing a substrate, the substrate contacts the bioreceptor or biomimic and reacts to generate a response which is detectable by the detection means and which is relatable to the concentration of the analyte, characterised in that the support comprises a non-volatile organic liquid having a vapour pressure no greater than 18 mmHg at 20° C. and a boiling point above 100° C.

2. A sensor according to claim 1 in which the non-volatile organic liquid is arranged in a layer having a thickness no greater than 5 mm.

3. A sensor according to claim 1 in which the detection means comprises an electrode on which the support is arranged whereby when the electrode is placed in a medium containing a substrate, the substrate can contact the bioreceptor or biomimic and react generating an electrical response.

4. A sensor according to claim 1 in which the detection means comprises a colour indicator and means for the indicator to interact with the bioreceptor or biomimic in the presence of the analyte.

5. A sensor according to claim 1 in which the support consists essentially only of the non-volatile organic liquid.

6. A sensor according to claim 1 in which the non-volatile organic liquid has an affinity for the analyte.

7. A sensor according to claim 1 in which the organic liquid has a viscosity of at least 10 cps at 20° C.

8. A sensor according to claim 1 in which the non-volatile organic liquid has a vapour pressure no greater than 10 mmHg at 20° C.

9. A sensor according to claim 1 in which the boiling point of the organic liquid is above 120° C.

10. A sensor according to claim 1 in which the support comprises at least 2% by weight (based on the weight of organic liquid) water.

11. A sensor according to claim 10 in which the organic liquid is water immiscible.

12. A sensor according to claim 1 in which the organic liquid comprises glycerol.

13. A sensor according to claim 1 in which the bioreceptor or biomimic is an enzyme.

14. A method for detecting an analyte comprising contacting a sensor according to claim 1 and measuring the response.

15. A method for detecting an analyte in a gaseous or vapor phase, comprising:
   placing a sensor in said gaseous or vapor phase, the sensor comprising a support, a bioreceptor or biomimic immobilized at the support, and a detection means,
   wherein the support comprises a non-volatile organic liquid having a vapor pressure no greater than 18 mmHg at 20° C. and a boiling point above 100° C.,
   contacting the analyte with the sensor, whereby a substrate is contacted with the bioreceptor or biomimic whereby a reaction of said substrate takes place in the support which generates a response,
   detecting the response by the detection means, and
   relating the response to a concentration of the analyte, wherein
   i) the analyte is the substrate,
   ii) the analyte is a precursor for the substrate which reacts at, or in, the support to form the substrate,
   iii) the analyte is an inhibitor of the reaction of the substrate at the bioreceptor or biomimic, or
   iv) the analyte is a precursor for an inhibitor of the reaction of the substrate at the bioreceptor or biomimic.

16. The method of claim 15, wherein the non-volatile organic liquid is arranged in a layer having a thickness no greater than 5 mm.

17. The method of claim 15, wherein the detection means comprises an electrode on which the support is arranged, whereby when the electrode is placed in a medium containing a substrate, the substrate can contact the bioreceptor or biomimic and react, generating an electrical response.

18. The method of claim 15, wherein the detection means comprises a color indicator and means for the indicator to interact with the bioreceptor or biomimic in the presence of the analyte.

19. The method of claim 15, wherein the support consists essentially of the non-volatile organic liquid.

20. The method of claim 15, wherein the non-volatile organic liquid has an affinity for the analyte.

21. The method of claim 15, wherein the organic liquid has a viscosity of at least 10 cps at 20° C.

22. The method of claim 15, wherein the non-volatile organic liquid has a vapor pressure no greater than 10 mmHg at 20° C.

23. The method of claim 15, wherein the boiling point of the organic liquid is above 120° C.

24. The method of claim 15, wherein the support comprises at least 2% by weight (based on the weight of organic liquid) water.

25. The method of claim 24, wherein the organic liquid is water immiscible.

26. The method of claim 15, wherein the organic liquid comprises glycerol.

27. The method of claim 15, wherein the bioreceptor or biomimic is an enzyme.

28. A method for detecting an analyte in a gaseous or vapor phase, comprising:

placing a sensor in said gaseous or vapor phase, the sensor comprising a support, a bioreceptor or biomimic immobilized at the support, and a detection means, wherein the support comprises a non-volatile organic liquid having a pressure no greater than 18 mmHg at 20° C. and a boiling point above 100° C., contacting the analyte with the bioreceptor or biomimic whereby a reaction takes place in the support which generates a response, detecting the response by the detection means, and relating the response to a concentration of the analyte.

29. A method for detecting an analyte in a gaseous or vapor phase, comprising:

placing a sensor in said gaseous or vapor phase, the sensor comprising a support, a bioreceptor or biomimic immobilized at the support, and a detection means, wherein the support comprises a non-volatile organic liquid having a vapor pressure of no greater than 18 mmHg at 20° C. and a boiling point of 100° C., reacting the analyte at, or in, the support to form a substrate, contacting the substrate with the bioreceptor or biomimic whereby a reaction of the substrate takes place in the support which generates a response, detecting the response by the detection means, and relating the response to a concentration of the analyte.

* * * * *